(12) United States Patent
Yamazaki

(10) Patent No.: US 7,555,097 B2
(45) Date of Patent: Jun. 30, 2009

(54) X-RAY COMPUTER TOMOGRAPHY SYSTEM

(75) Inventor: Masahiko Yamazaki, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/464,027

(22) Filed: Aug. 11, 2006

(65) Prior Publication Data

US 2007/0071162 A1 Mar. 29, 2007

(30) Foreign Application Priority Data

Sep. 28, 2005 (JP) ............................. 2005-281702

(51) Int. Cl.
*H05G 1/64* (2006.01)
*G01N 23/083* (2006.01)

(52) U.S. Cl. ........................................ 378/19

(58) Field of Classification Search ............... 378/4, 378/19, 62, 98.8; 250/370.09, 370.11; 600/425
See application file for complete search history.

(56) References Cited

U.S. PATENT DOCUMENTS

| | | | |
|---|---|---|---|
| 5,510,622 A | | 4/1996 | Hu et al. |
| 5,781,606 A | * | 7/1998 | Dobbs et al. ................. 378/19 |
| 5,815,546 A | * | 9/1998 | Flohr et al. .................. 378/19 |
| 5,834,782 A | * | 11/1998 | Schick et al. ........... 250/370.11 |
| 6,118,840 A | | 9/2000 | Toth et al. |
| 6,118,841 A | * | 9/2000 | Lai .............................. 378/19 |
| 6,324,246 B1 | * | 11/2001 | Ruimi ......................... 378/15 |
| 6,341,156 B1 | * | 1/2002 | Baetz et al. ................ 378/98.8 |
| 6,403,964 B1 | * | 6/2002 | Kyyhkynen ............ 250/370.09 |
| 6,744,844 B2 | * | 6/2004 | Horiuchi ...................... 378/15 |
| 6,947,516 B2 | | 9/2005 | Okumura et al. |
| 2002/0054659 A1 | | 5/2002 | Okumura et al. |

FOREIGN PATENT DOCUMENTS

| | | | |
|---|---|---|---|
| GB | 2278765 A | * | 12/1994 |
| WO | WO 98/04193 | | 2/1998 |
| WO | WO 2006/035328 A1 | | 4/2006 |

* cited by examiner

*Primary Examiner*—Edward J Glick
*Assistant Examiner*—Thomas R Artman
(74) *Attorney, Agent, or Firm*—Oblon, Spivak, McClelland, Maier & Neustadt, P.C.

(57) ABSTRACT

There is disclosed an X-ray computer tomography system having an X-ray tube for producing X-rays, an X-ray detector including plural detector modules, a rotation mechanism by which the X-ray tube and the X-ray detector are held so as to be rotatable about an axis of rotation, a reconstruction unit for reconstructing images based on the output from the detector, and a display unit for displaying the reconstructed images. Each of the detector modules has plural detector elements arranged in a matrix. The detector elements act to detect the X-rays transmitted through a subject to be examined. The detector modules are arranged along a reference axis substantially perpendicular to the axis of rotation and tilted relative to the axis of rotation.

10 Claims, 8 Drawing Sheets

SLICE DIRECTION

CHANNEL DIRECTION

X-RAY COMPUTER TOMOGRAPHY SYSTEM

CROSS-REFERENCE TO RELATED APPLICATIONS

This application is based upon and claims the benefit of priority from prior Japanese Patent Application No. 2005-281702, filed Sep. 28, 2005, the entire contents of which are incorporated herein by reference.

BACKGROUND OF THE INVENTION

1. Field of the Invention

The present invention relates to an X-ray computer tomography system equipped with two-dimensional arrays of X-ray detectors.

2. Description of the Related Art

A multi-slice X-ray computer tomography system is equipped with a detector in which a plurality of rows of detector elements are juxtaposed in the slice direction. A still improved, so-called two-dimensional array of detectors has appeared. In particular, plural detector modules are arrayed in the direction of channel. Each detector module consists of a matrix of semiconductor detector elements formed on a substrate.

In these X-ray detectors, contrivances are often made to shorten the apparent center-to-center distance (actual spatial resolution) between detector elements adjacent to each other in the direction of channel. One contrivance is to adopt an offsetting means for offsetting the center position of the detector relative to the slice centerline connecting the focal point of X-rays and the axis of rotation by a distance equal to a fraction of the channel pitch. Another is to adopt a zigzaggedly combtoothed collimator.

However, where the offsetting means is used, the apparent resolution can be improved only up to a half of the actual resolution. Even where the offsetting means is used in combination with the zigzaggedly combtoothed collimator, the apparent resolution can be improved only up to a quarter of the actual resolution. Where the zigzaggedly combtoothed collimator is adopted, the light reception efficiency decreases in inverse proportion to increase in the shielded area caused by the used collimator. In other words, the sensitivity is deteriorated.

BRIEF SUMMARY OF THE INVENTION

It is an object of the present invention to provide an X-ray computer tomography system equipped with a multi-slice X-ray detector or a two-dimensional array X-ray detector, the system being capable of greatly improving the spatial resolution intrinsic to the X-ray detector by a simple structural modification.

A first aspect of the present invention provides an X-ray computer tomography system having an X-ray tube for producing X-rays, an X-ray detector including plural detector modules, a support mechanism by which the X-ray tube and the X-ray detector are held so as to be rotatable about an axis of rotation, a reconstruction unit for reconstructing images based on the output from the X-ray detector, and a display portion for displaying the reconstructed images. Each of the detector modules has a matrix of detector elements for detecting X-rays transmitted through a subject to be examined. The detector modules are arranged along a reference axis substantially perpendicular to the axis of rotation, and are tilted relative to the axis of rotation.

A second aspect of the present invention provides an X-ray computer tomography system having an X-ray tube for producing X-rays, an X-ray detector for detecting X-rays transmitted through a subject to be examined, a support mechanism by which the X-ray tube and the X-ray detector are held so as to be rotatable about an axis of rotation, a reconstruction unit for reconstructing images based on the output from the X-ray detector, and a display portion for displaying the reconstructed images. The X-ray detector is tilted relative to the axis of rotation.

A third aspect of the present invention provides an X-ray computer tomography system having an X-ray tube for producing X-rays, an X-ray detector for detecting X-rays transmitted through a subject to be examined, a support mechanism by which the X-ray tube and the X-ray detector are held so as to be rotatable about an axis of rotation, a reconstruction unit for reconstructing images based on the output from the X-ray detector, and a display portion for displaying the reconstructed images. The X-ray detector has plural detector elements arranged in rows and columns. Each of the detector elements has a substantially parallelogrammatic light-sensitive region.

A fourth aspect of the present invention provides an X-ray computer tomography system having an X-ray tube for producing X-rays, an X-ray detector for detecting X-rays transmitted through a subject to be examined, a support mechanism by which the X-ray tube and the X-ray detector are held so as to be rotatable about an axis of rotation, a reconstruction unit for reconstructing images based on the output from the X-ray detector, and a display portion for displaying the reconstructed images. The X-ray detector has plural detector elements arranged in rows and columns. Each of the detector elements has a scintillator chip having a substantially parallelogrammatic planar geometry.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments of the present invention are hereinafter described with reference to the drawings. To reconstruct one slice of tomographic image data by an X-ray computer tomography system, projection data about one revolution (approximately 360°) around a subject to be examined are necessary. Furthermore, where the half scanning technique is used, projection data about 180°+fan angle are necessary. The present invention can be applied to either reconstruction method.

Figure 1:
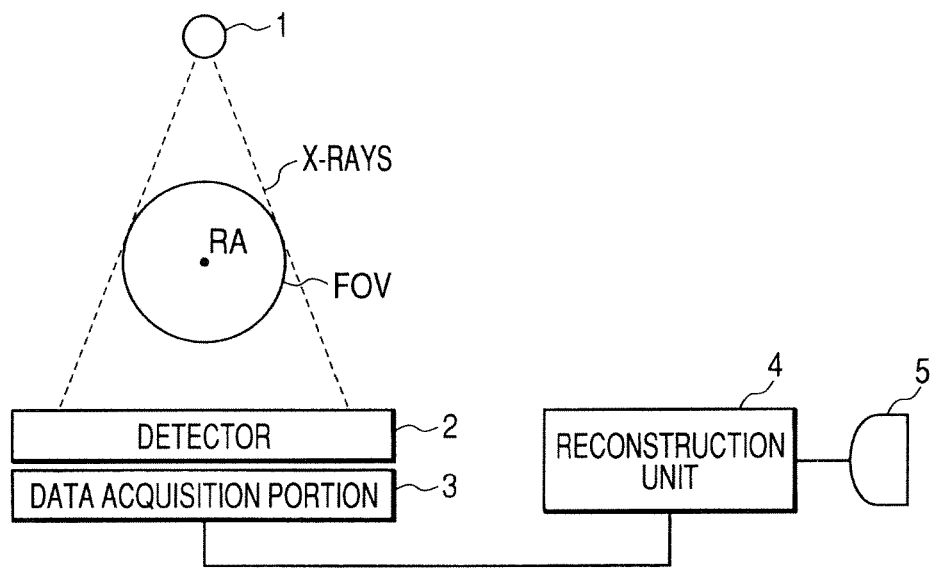
FIG. 1 is a block diagram showing the configuration of a main portion of an X-ray computer tomography system according to an embodiment of the present invention.

FIG. 1 shows the configuration of an X-ray computer tomography system associated with the present embodiment. The system has an X-ray tube 1 for producing X-rays and an X-ray detector 2 for detecting the X-rays transmitted through a subject to be examined. The X-ray tube 1 and the X-ray detector 2 are supported to a support mechanism (not shown) such that the tube and detector can rotate about an axis of rotation RA while the tube and detector are maintained in mutually opposite positional relationship. The detector 2 is opposite to the X-ray tube 1. When a tube voltage is continuously or intermittently applied to the X-tube 1 from a high voltage-generating device (not shown) via a slip ring during rotation, X-rays are emitted from the X-ray tube 1 continuously or intermittently.

A data collection portion 3 that is generally known as a data acquisition system (DAS) converts the output signal corresponding to each channel from the X-ray detector 2 into a voltage signal, amplifies it, and converts the signal into a digital signal. The raw data are sent through a noncontacting data transfer device (not shown) and then to a pretreatment device accommodated within a console mounted outside the gantry. In the pretreatment device, the signal undergoes a correction operation such as sensitivity correction. Then, the data are sent as so-called projection data to a reconstruction unit 4. The reconstruction unit 4 reconstructs data about a spatial distribution of X-ray absorption coefficients (hereinafter referred to simply as the images) in a slice or volume based on the projection data. The data are sent to a display device 5, arbitrarily processed such as cross section conversion (MPR), and displayed as images.

Figure 2:
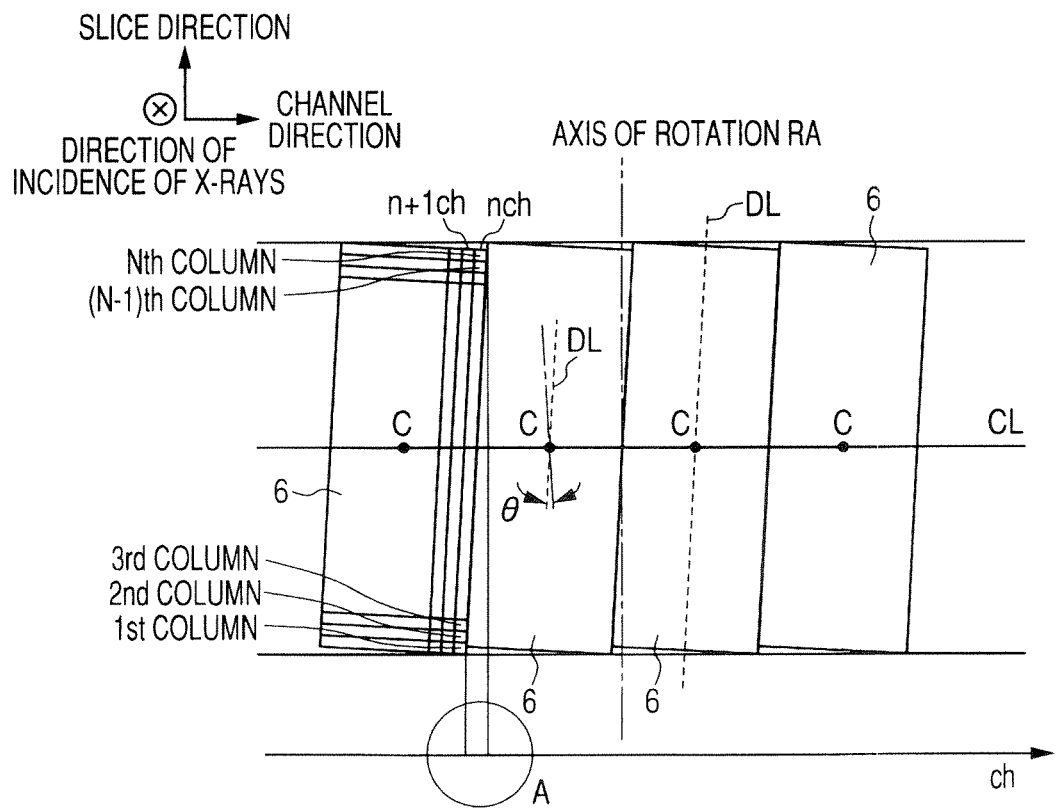
FIG. 2 is a plan view showing the array of plural detector modules constituting the X-ray detector of FIG. 1.
Figure 3A:
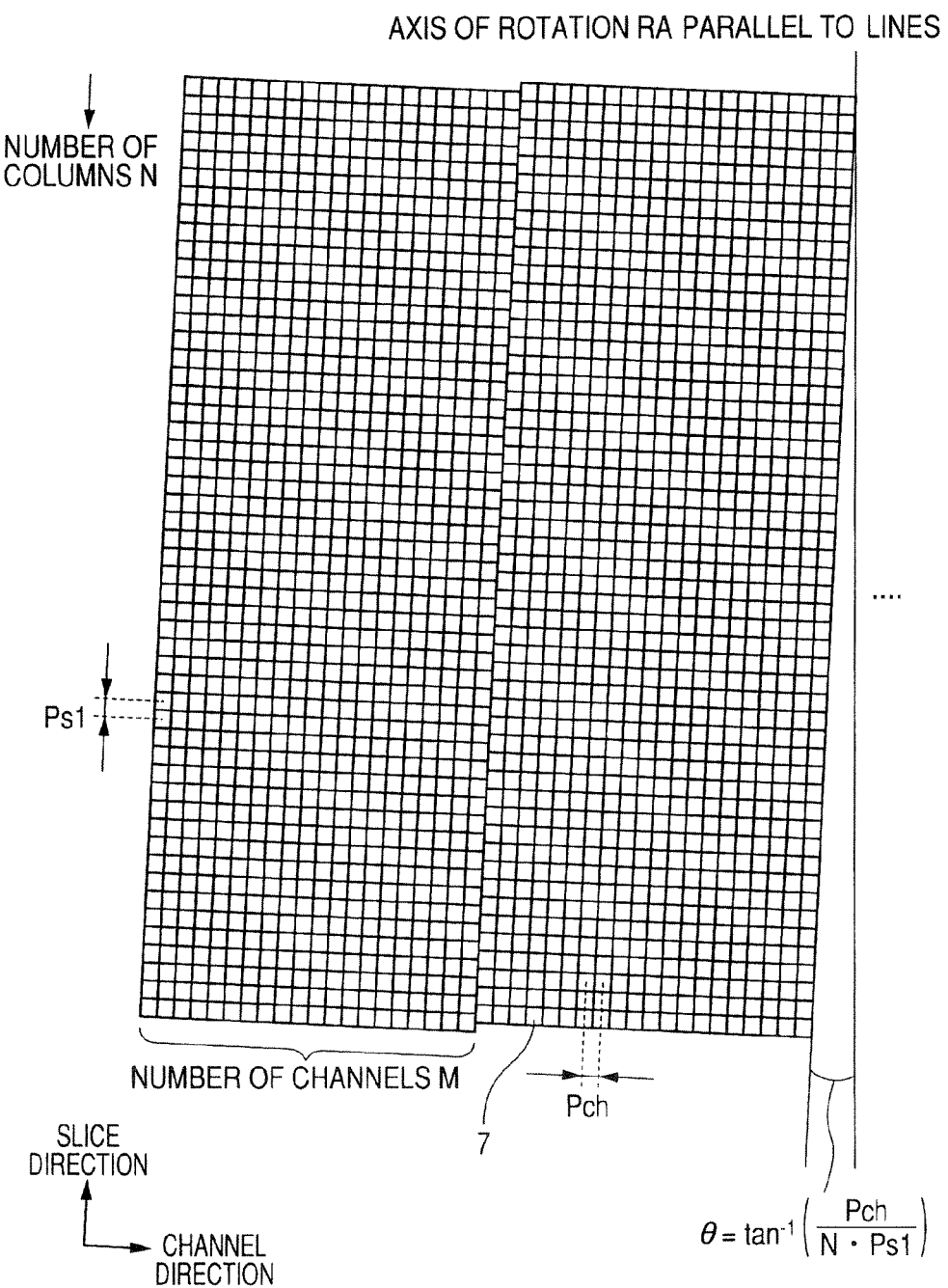
FIG. 3A is a detailed view of the detector modules of FIG. 2.

A planar structure of the X-ray detector 2 of FIG. 1 is shown in FIGS. 2 and 3A. The detector 2 has plural detector modules 6, each of which has plural detector elements 7 arranged in rows and columns. The plural detector elements 7 are arranged regularly at a constant center-to-center spacing (channel pitch) in one direction (channel direction). The center-to-center distance (channel pitch) between the detector elements 7 adjacent to each other in this one direction (channel direction) is denoted by Pch. The plural detector elements 7 are regularly arranged at a constant center-to-center spacing (slice pitch) in the other direction (slice direction) perpendicular to the channel direction. The center-to-center distance (slice pitch) of the detector elements 7 adjacent to each other in the other direction (slice direction) is denoted by Psl.

Figure 3B:
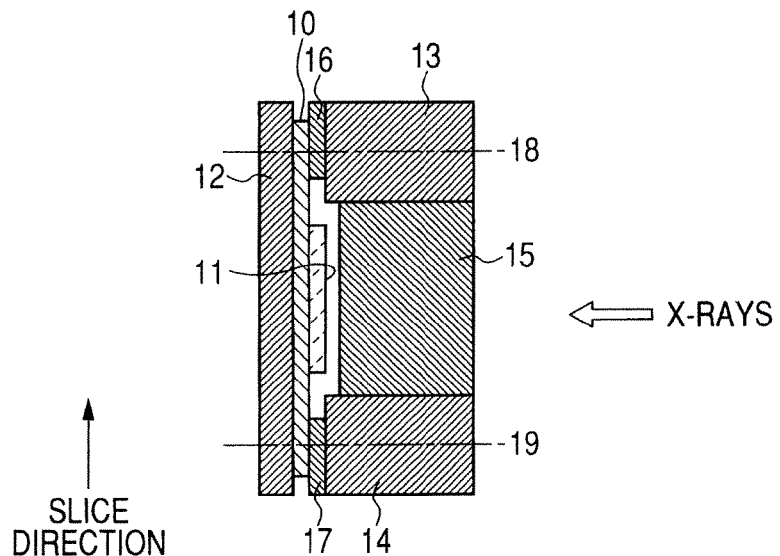
FIG. 3B is a horizontal cross section of the X-ray detector of FIG. 1.

As shown in FIG. 3B, each of the detector modules 6 consists of a single photodiode array substrate 10 and a single scintillator plate 11 mounted on the surface of the substrate 10. The scintillator plate 11 converts incident X-rays into light. A matrix of photodiodes are formed on the surface of the photodiode array substrate 10. Typically, one photodiode forms one channel. Each detector module 6 is sandwiched among support blocks 13, 14 and a back plate 12 and fixed with screws 20. If necessary, spacers 16 and 17 are disposed between the support blocks 13 and 14, respectively, and the substrate 10 of the detector module 6. As described later, the centerline DL of the detector module 6 is tilted relative to the axis of rotation RA. The centerline DL is a line which passes through the center C of the detector module 6 and is parallel to the longitudinal axis of the photodiode array. The centerline DL is defined as the symmetrical line of the photodiode array. Typically, the angle of tilt θ of the centerline DL of each detector module 6 relative to the axis of rotation RA is constant. However, the angle of tilt θ of the centerline DL of each detector module 6 relative to the axis of rotation RA does not need to be constant. For example, the angle of tilt θ of the centerline DL of each detector module 6 relative to the axis of rotation RA may be smallest in the center of array and increase toward either end. The angle of tilt θ of the centerline DL of each detector module 6 relative to the axis of rotation RA may be greatest in the center of array and decrease toward either end.

Figure 3C:
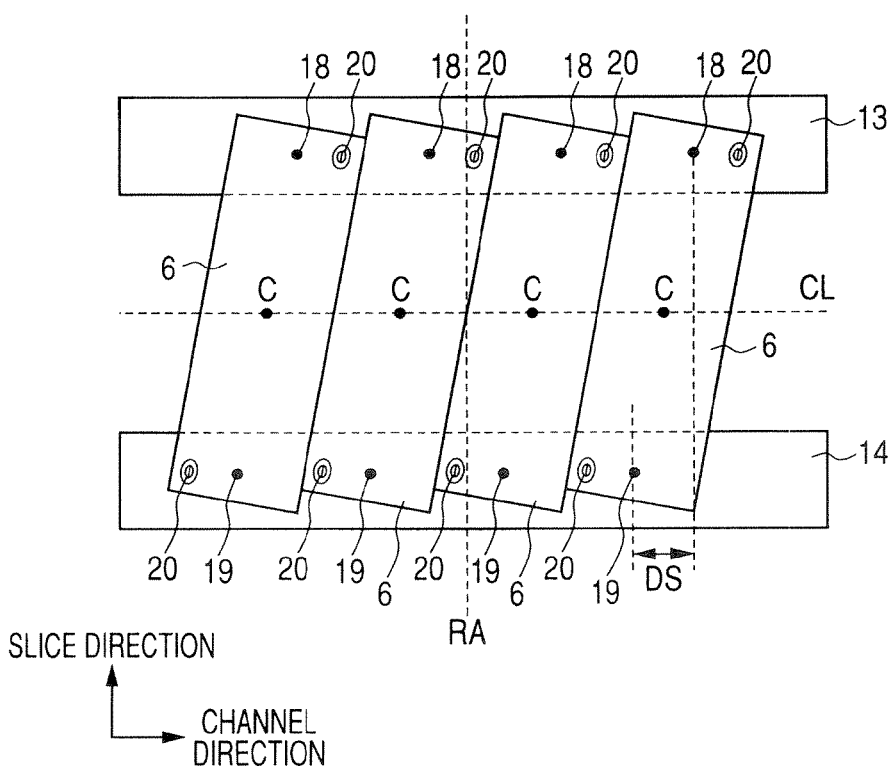
FIG. 3C is a plan view showing the manner in which detector modules are mounted to a support member from the rear side under the condition where the back plate of FIG. 3B has been removed.

As shown in FIG. 3C, positioning holes 18 are formed in one support block 13 at regular intervals. Positioning holes 19 are formed in the other support block 14 at the same intervals. Similar holes are formed also in the spacers 16, 17, substrate 10, and back plate 12. Positioning pins are inserted in the holes to improve the positioning accuracy. The positioning holes 19 and the positioning holes 18 make pairs. The holes 19 are shifted in the direction perpendicular to the axis of rotation RA by a distance DS corresponding to the angle of tilt of each detector module 6.

The detector modules 6 are arranged along the channel direction perpendicular to the axis of rotation RA. The centerline DL of each module 6 is tilted at a given angle (angle selected, for example, from a range from 2° to 10°) relative to the axis of rotation RA or a line substantially parallel to it. Additionally, the plural detector modules 6 are arranged along a reference line CL perpendicular to the axis of rotation RA. Furthermore, each detector module 6 is so arranged that its center position C is located on the reference line CL. As shown in FIG. 3C, the positions where the detector modules 6 are mounted relative to the slice direction are designed according to the angle of tilt.

Let N be the number of rows of the elements of the X-ray detector 2. The angle of tilt is set to $$\tan^{-1}\left(\frac{Pch}{m \cdot Psl}\right)$$

where Pch is the center-to-center distance (channel pitch) between detector elements adjacent to each other in the channel direction, Psl is the center-to-center distance (slice pitch) between detector elements adjacent to each other in the slice direction, and m is an integer that is greater than 2 and less than N. The highest apparent spatial resolution is achieved when m=N, i.e., when the angle of tilt is given by $$\tan^{-1}\left(\frac{Pch}{N \cdot Psl}\right)$$

Figure 4:
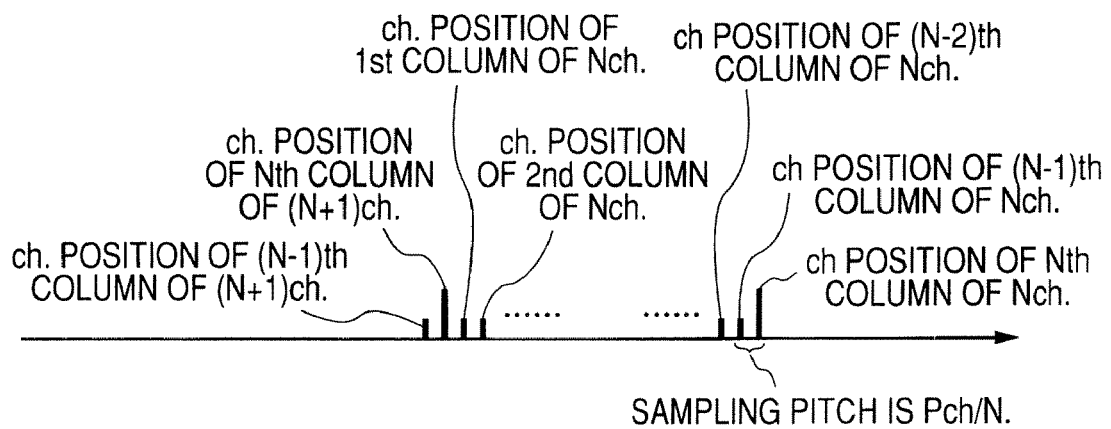
FIG. 4 is a detailed view of portion A of FIG. 2.

As shown in FIG. 4, the highest apparent spatial resolution is given by $$\frac{Pch}{N}$$

That is, the spatial resolution can be reduced to 1/N of the actual spatial resolution Pch of the detector 2. In other words, the apparent resolution is improved to a value higher than the actual resolution of the detector 2 by a factor of N. If a QQ offset means for offsetting the center position of the detector relative to the projection centerline connecting the focal point of X-rays and the axis of rotation RA by a distance equal to a fraction of the channel pitch Pch is used in combination, the apparent spatial resolution can be reduced to 1/(2·N), and the apparent resolution can be improved by a factor of (2·N).

The plural detector modules 6 may be arrayed in a line in the same way as in the prior art and the whole X-ray detector 2 may be tilted relative to the axis of rotation RA by a predetermined angle of tilt.

Figure 5:
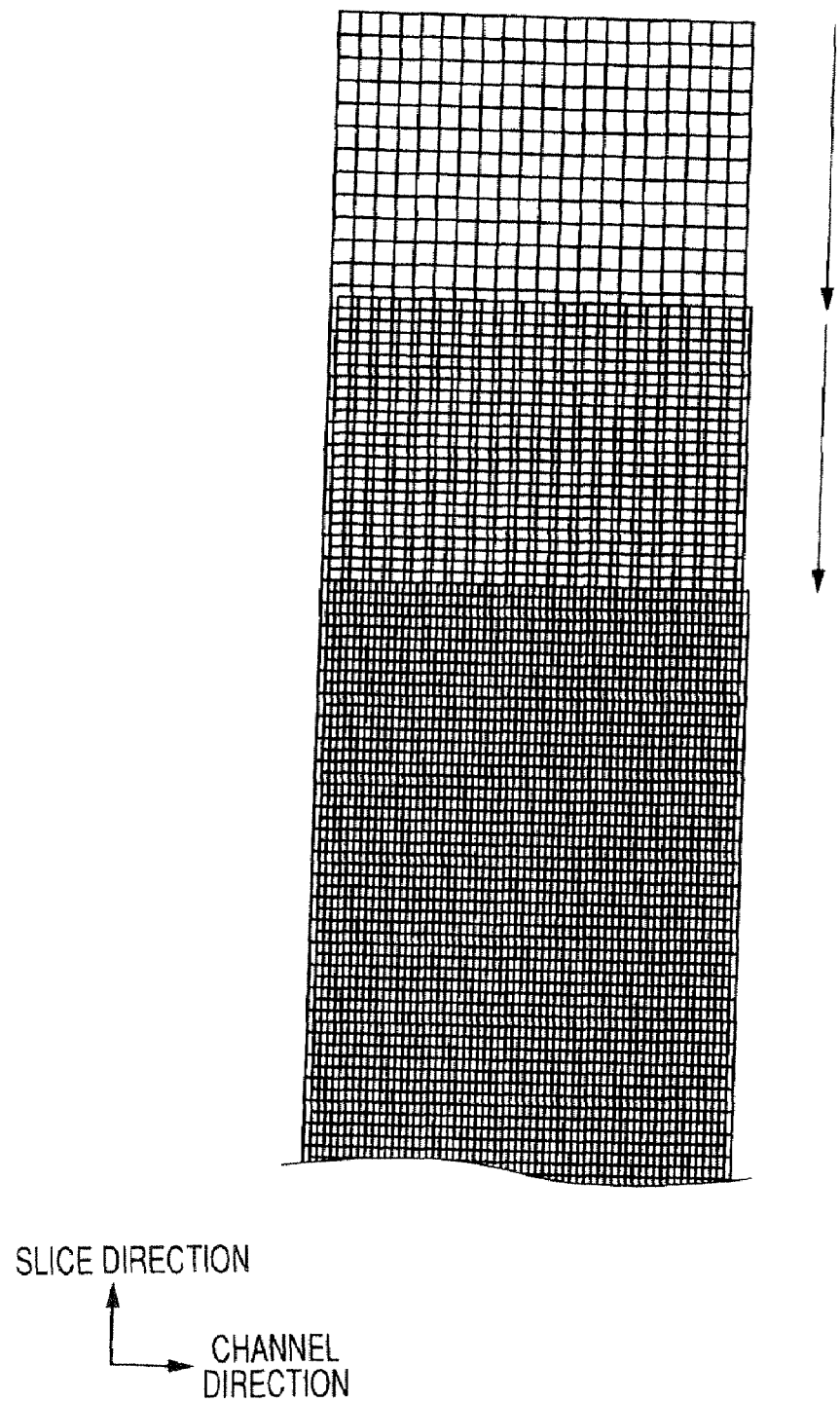
FIG. 5 is a view supplementarily illustrating improvement of the apparent spatial resolution in the overlap helical scanning mode in the present embodiment.
Figure 6:
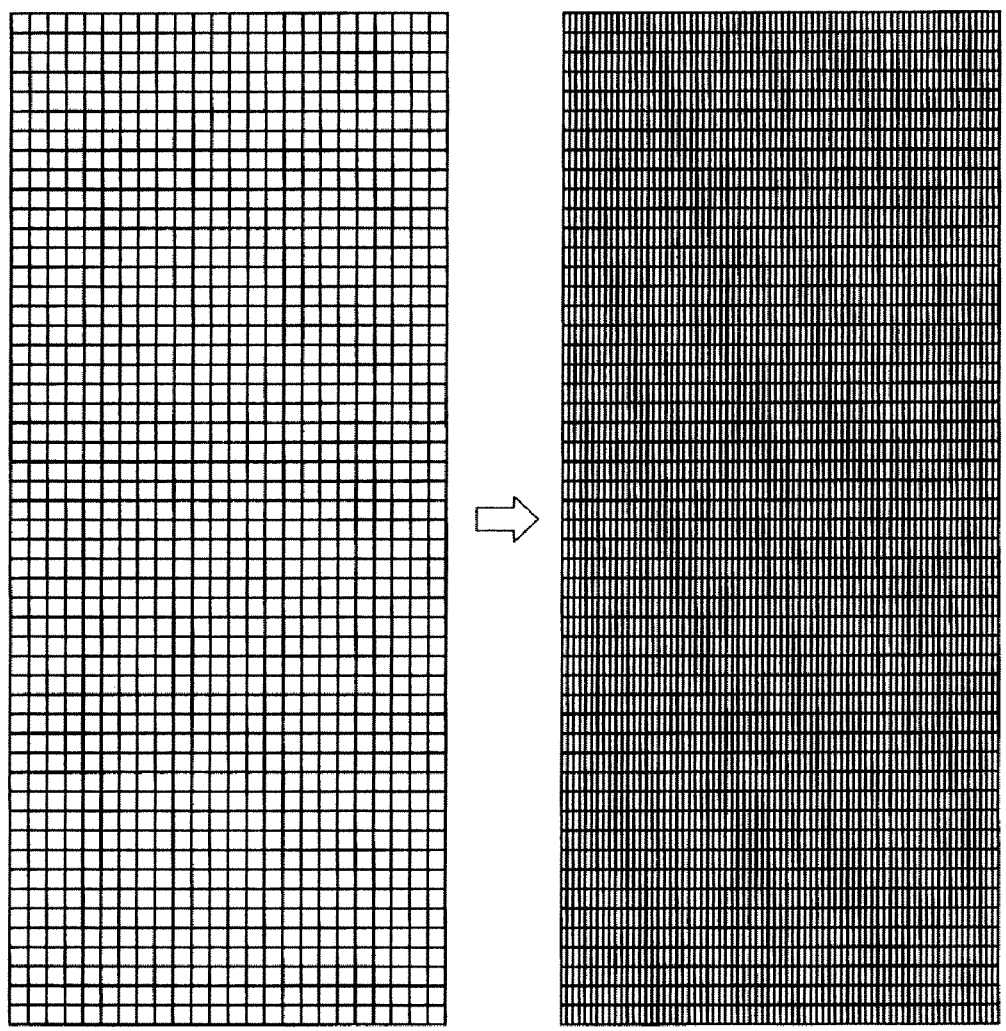
FIG. 6 is a diagram illustrating the apparent spatial resolution corresponding to FIG. 5.
Figure 6:
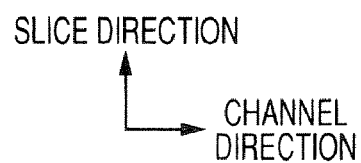

In the helical scanning mode, too, the helical pitch (distance traveled by the top plate per revolution) is set such that partial overlap occurs as shown in FIG. 5. Thus, the apparent spatial resolution in the overlapped portions can be reduced to 1/m and the apparent resolution can be improved by a factor of 2·m, as shown in FIG. 6. Furthermore, the apparent spatial resolution can be reduced to 1/(2·N) and the apparent resolution can be improved by a factor of 2·N by optimizing the helical pitch to {Psl×(N−1)}/N.

Figure 7:
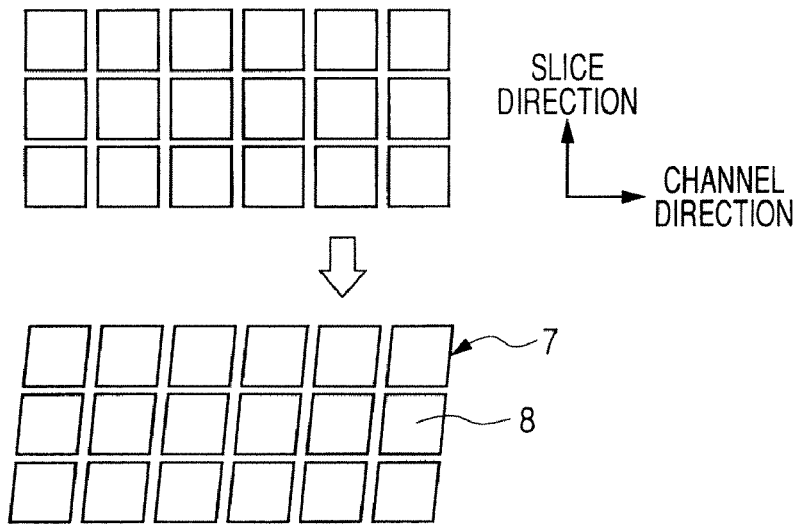
FIG. 7 is a diagram illustrating a modified example of detector elements of FIG. 3.
Figure 8:
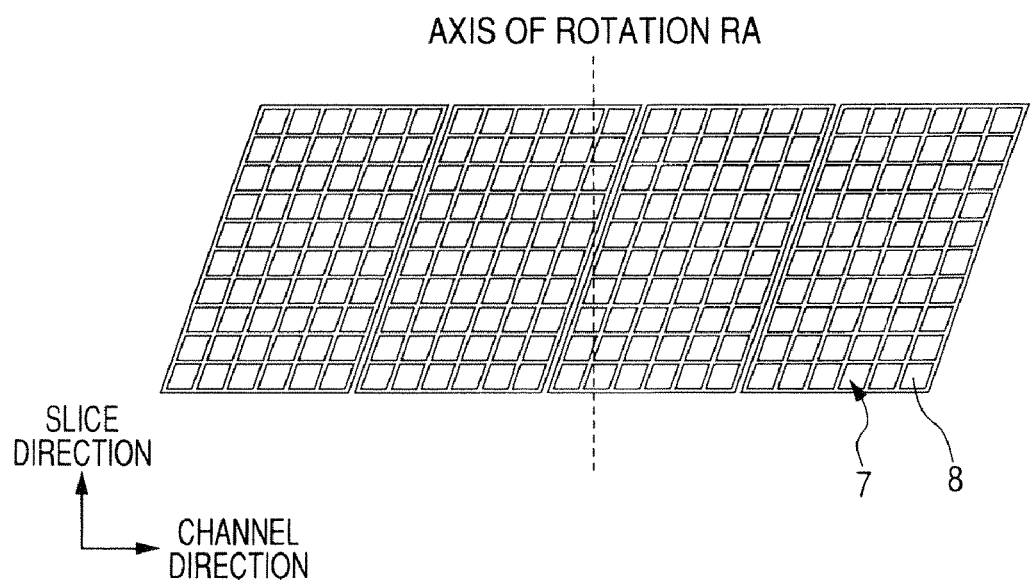
FIG. 8 is a plan view of the whole detector corresponding to FIG. 7.

Similar effect can be produced by shaping the light-sensitive region of each detector element 7, i.e., the planar geometry of the scintillator chip 8, into a parallelogram, as shown in FIGS. 7 and 8, tilted by an angle of tilt given by $$\tan^{-1}\left(\frac{Pch}{N \cdot Psl}\right)$$

Figure 9:
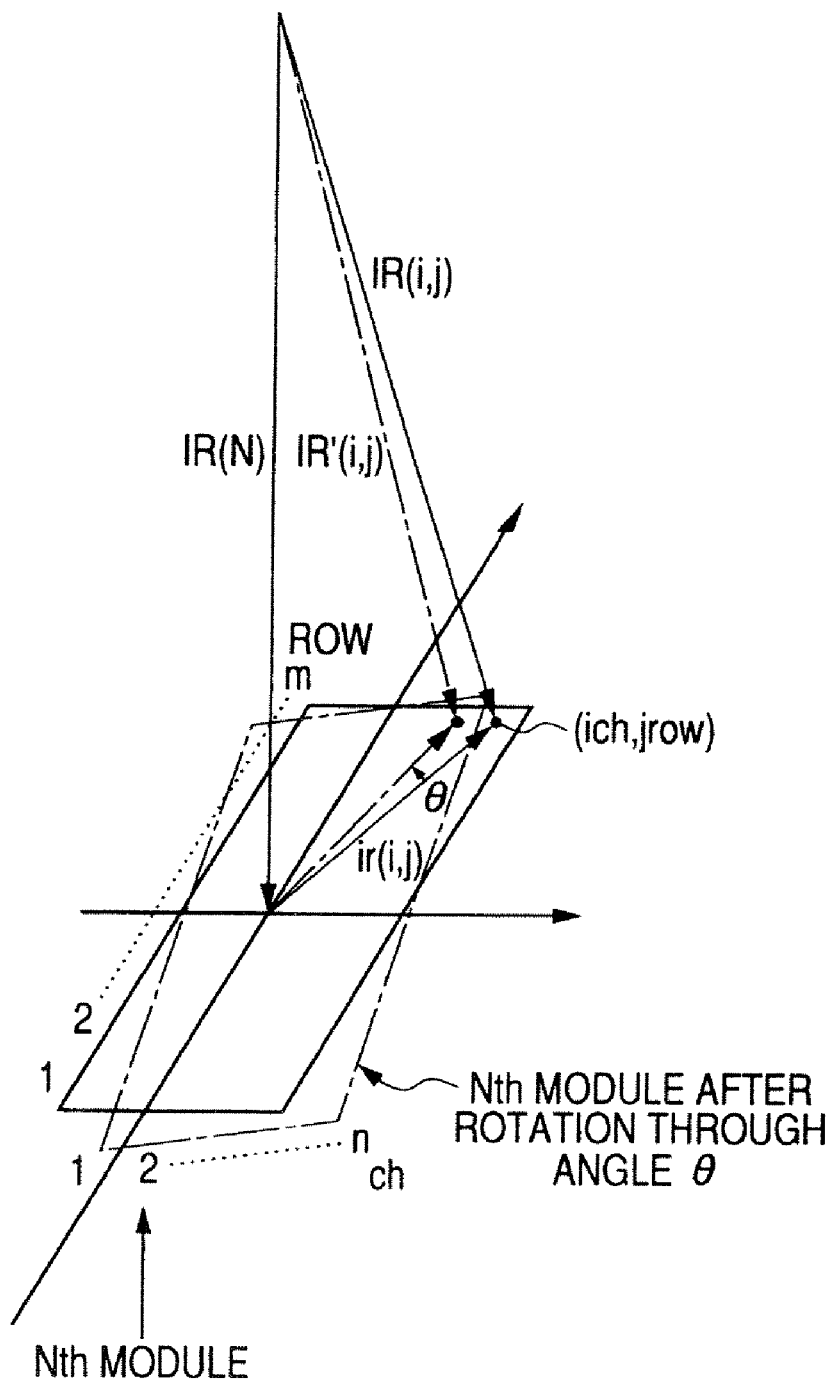
FIG. 9 is a view illustrating coordinate conversion involved in tilting detector modules of the reconstruction unit of FIG. 1.

Because of the tilt of the modules 6, it is almost unnecessary to improve the processing for reconstruction. As shown in FIG. 9, it is only necessary to perform coordinate conversions as a pretreatment for the reconstruction. A positional vector R of each element (channel) when there is no tilt is given by $$R(i,j)=R(N)+r(i,j)$$

where N is a module number, i is a channel number, and j is a row number.

Let θ be the angle of tilt. Let M (N,θ) be a rotation matrix when the sensitive surface of module number N is rotated through an angle of rotation θ. The positional vector R' of each rotated element is given by $$R'(i,j)=R(N)+M(N,\theta) \cdot r(i,j)$$

At the position of the converted positional vector R'(i,j) of each element, back projection is performed during cone-beam reconstruction. The back projection is the same as the processing performed heretofore. As a result, volume data can be obtained.

As described so far, according to the present embodiment, the spatial resolution intrinsic to the detector can be improved greatly by a simple structural modification consisting of mounting the X-ray detector or detector modules at an angle to the axis of rotation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computer tomography system comprising:
   an X-ray tube for producing X-rays;
   an X-ray detector having a plurality of detector modules each having a plurality of detector elements arranged in a matrix, the detecting elements being adapted to detect X-rays transmitted through a subject to be examined;
   a support mechanism by which the X-ray tube and the X-ray detector are held so as to be rotatable about an axis of rotation;
   a reconstruction unit for reconstructing images based on an output from the X-ray detector; and
   a display portion for displaying the reconstructed images;
   wherein each of the detector modules is arranged along a reference axis substantially perpendicular to the axis of rotation and individually tilted relative to the axis of rotation by an angle of tilt, and
   the detector modules are arranged such that each detector module is fixed at a contact point which is offset a distance from the contact point of an adjacent detector module.

2. The X-ray computer tomography system of claim 1, wherein said detector modules are tilted at a given angle to said axis of rotation.

3. The X-ray computer tomography system of claim 1, wherein said detector modules have their center located on said reference axis.

4. The X-ray computer tomography system of claim 1, wherein said angle of tilt is set to $$\tan^{-1}\left(\frac{Pch}{N \cdot Psl}\right)$$

where N is the number of columns in the X-ray detector, Pch is the center-to-center distance between the detector elements adjacent to each other along a reference line, and Psl is the center-to-center distance between the detector elements adjacent to each other along said axis of rotation.

5. The X-ray computer tomography system of claim 1, wherein said angle of tilt is set to $$\tan^{-1}\left(\frac{Pch}{m \cdot Psl}\right)$$

where N is the number of columns in the X-ray detector, Pch is the center-to-center distance between the detector elements adjacent to each other along a reference line, Psl is the center-to-center distance between the detector elements adjacent to each other along said axis of rotation, and m is an integer that is not less than 2 and not more than N.

6. The X-ray computer tomography system of claim 1, wherein each of said detector modules has a substrate, a photodiode array formed on the substrate, and a scintillator plate disposed over the photodiode array.

7. The X-ray computer tomography system of claim 1, wherein said detector modules are sandwiched among a pair of support blocks and a back plate.

8. The X-ray computer tomography system of claim 7, wherein plural collimator plates are laid between said one pair of support blocks.

9. The X-ray computer tomography system of claim 7, wherein said one pair of support blocks is provided with plural pairs of positioning holes which have been shifted by a given distance with respect to said reference line.

10. The X-ray computer tomography system of claim 1, wherein said reconstruction unit has a function of converting coordinates of the position of each of said detector elements by a rotation matrix corresponding to the angle of tilt of said detector modules.

\* \* \* \* \*